United States Patent
Houtz (10) Patent No.: US 8,138,309 B2
(45) Date of Patent: Mar. 20, 2012

(54) MODIFIED RUBISCO LARGE SUBUNIT N-METHYLTRANSFERASE USEFUL FOR TARGETING MOLECULES TO THE ACTIVE-SITE VICINITY OF RIBULOSE-1,5-BISPHOSPHATE

(75) Inventor: Robert L. Houtz, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 890 days.

(21) Appl. No.: 12/190,246

(22) Filed: Aug. 12, 2008

(65) Prior Publication Data

US 2009/0070901 A1 Mar. 12, 2009

(51) Int. Cl.
*C07K 14/00* (2006.01)
(52) U.S. Cl. ...................................................... 530/350
(58) Field of Classification Search .................... 530/350
See application file for complete search history.

*Primary Examiner* — Maryam Monshipouri
(74) *Attorney, Agent, or Firm* — Crowell & Moring LLP (57) ABSTRACT

The present invention generally relates to a modified Rubisco large subunit $\epsilon$N-Methyltransferase (Rubisco LSMT, or RLSMT). The present invention also relates to a modified RLSMT-carbonic anhydrase (RLSMT-CA). This modified RLSMT-CA improves the efficiency of the reduction of $CO_2$ during photosynthesis, which may increase plant growth rates. The present invention also relates to nucleic acids encoding the modified RLSMT-CA or modified RLSMT. Also, the present invention relates to cells including the modified RLSMT-CA or modified RLSMT, plants containing the modified RLSMT-CA or modified RLSMT, and methods using compositions of the present invention. In addition, the present invention relates to antibodies conjugated to CA which may bind to Rubisco, and antibodies which bind a modified RLSMT-CA. The invention also relates to modified forms of the LS and SS of Rubisco where the modified forms are fusions with CA or biologically active fragments thereof. The present invention provides methods of altering Rubisco carboxylase activity and altering plant growth.

14 Claims, 6 Drawing Sheets

SEQ ID No. 1
atg g caaaatcagt
agcctctgta ggaaccgaac catcactgtc tccagcagtt caaaccttct ggaagtggct
acaggaagaa ggtgtcatca ctgcaaagac cccagtgaaa gctagtgtgg tcacagaagg
tttaggattg gttgcactta aggacatttc taggaatgat gttattttgc aggtaccaaa
aaggctgtgg ataaatccag atgcagttgc agcttcagag attggagag tgtgcagtga
gttgaagcca tggttgtctg ttatactctt tcttataaga gagaggtcaa gggaagattc
tgtttggaag cactattttg gtattctgcc acaggaaact gattctacta tatattggtc
agaggaagag cttcaagagc ttcaaggttc tcaacttttg aaaacaacag tgtctgtgaa
agaatatgtg aagaatgaat gtttgaaact agaacaagaa atcattctcc ctaataagcg
gcttttccg gatcctgtga cgctggatga cttcttttgg gcatttgaa ttctcagatc
aagggcgttt tctcgccttc gcaatgaaaa tctggttgtg gttccaatgg cagacttgat
taaccacagt gcaggagtta ctacagagga tcatgcttat gaagttaaag gagcagctgg
ccttttctct tgggattacc tatttttcctt aaagagcccc ctttccgtca aggccggaga
acaggtatat atacaatatg atttgaacaa aagcaatgca gagttggctc tagactacgg
tttcattgaa ccaaatgaaa atcgacatgc atacactctg acgctggaga tatctgagtc
ggaccctttt tttgatgaca aactagacgt tgctgagtcc aatggttttg ctcagacagc
gtactttgac atcttctata atcgcactct tccacctgga ttgcttccat atctgagact
tgtagcgcta gggggtaccg acgctttctt attggaatca ctgttcagag acaccatatg
gggtcatctt gagttgtctg tcagccgtga caatgaggag ctactatgca aagccgttcg
agaagcctgc aaatctgccc ttgctggtta tcatacaacc attgaacagg atcgcgagtt
gaaagaagga aatctagatt caaggcttgc aatagcagtt ggaataagag aaggggaaaa
gatggtcctg cagcaaattg acgggatctt cgagcagaaa gaattggagt tggaccagtt
agagtattat caagaaagga ggctcaagga tcttggactt tgcggagaaa atggcgatat
ccttggagac ctaggaaaat tcttc
ctcgaa ggc gga ggc ggg agc gcg gcc gcg ggc agc ctc gag
tc ccatcactgg gggtacggca acacaacgg acctgagcac tggcataagg
acttccccat gccaaggga gagcgccagt cccctgttga catcgacact catacagcca
agtatgaccc ttccctgaag cccctgtctg tttcctatga tcaagcaact tccctgagga
tcctcaacaa tggtcatgct ttcaacgtgg agtttgatga ctctcaggac aaagcagtgc
tcaagggagg acccctggat ggcacttaca gattgattca gtttcacttt cactggggtt
cacttgatgg acaaggttca gagcatactg tggataaaaa gaaatatgct gcagaacttc
acttggttca ctggaacacc aaatatgggg attttgggaa agctgtgcag caacctgatg
gactggccgt tctaggtatt ttttgaagg ttggcagcgc taaaccggc cttcagaaag
ttgttgatgt gctggattcc attaaaacaa agggcaagag tgctgacttc actaacttcg
atcctcgtgg cctccttcct gaatccctgg attactggac ctaccaggc tcactgacca
cccctcctct tctggaatgt gtgacctgga ttgtgctcaa ggaacccatc agcgtcagca
gcgagcaggt gttgaaattc cgtaaactta acttcaatgg ggagggtgaa cccgaagaac
tgatggtgga caactggcgc ccagctcagc cactgaagaa caggcaaatc aaagcttcct
tcaaataa Fig. 6B
SEQ ID No. 2

```
  1 MAKSVASVGT EPSLSPAVQT FWKWLQEEGV ITAKTPVKAS VVTEGLGLVA LKDISRNDVI   60
 61 LQVPKRLWIN PDAVAASEIG RVCSELKPWL SVILFLIRER SREDSVWKHY FGILPQETDS  120
121 TIYWSEEELQ ELQGSQLLKT TVSVKEYVKN ECLKLEQEII LPNKRLFPDP VTLDDFFWAF  180
181 GILRSRAFSR LRNENLVVVP MADLINHSAG VTTEDHAYEV KGAAGLFSWD YLFSLKSPLS  240
241 VKAGEQVYIQ YDLNKSNAEL ALDYGFIEPN ENRHAYTLTL EISESDPFFD DKLDVAESNG  300
301 FAQTAYFDIF YNRTLPPGLL PYLRLVALGG TDAFLLESLF RDTIWGHLEL SVSRDNEELL  360
361 CKAVREACKS ALAGYHTTIE QDRELKEGNL DSRLAIAVGI REGEKMETVL QQIDGIFEQK  420
421 ELELDQLEYY QERRLKDLGL CGENGDILGD LGKFFLEGGG GSAAAGSLES HHWGYGKHNG  480
481 PEHWHKDFPI AKGERQSPVD IDTHTAKYDP SLKPLSVSYD QATSLRILNN GHAFNVEFDD  540
541 SQDKAVLKGG PLDGTYRLIQ FHFHWGSLDG QGSEHTVDKK KYAAELHLVH WNTKYGDFGK  600
601 AVQQPDGLAV LGIFLKVGSA KPGLQKVVDV LDSIKTKGKS ADFTNFDPRG LLPESLDYWT  660
661 YPGSLTTPPL LECVTWIVLK EPISVSSEQV LKFRKLNFNG EGEPEELMVD NWRPAQPLKN  720
721 RQIKASFK
```

MODIFIED RUBISCO LARGE SUBUNIT N-METHYLTRANSFERASE USEFUL FOR TARGETING MOLECULES TO THE ACTIVE-SITE VICINITY OF RIBULOSE-1,5-BISPHOSPHATE

This work was supported by the U.S. Department of Energy grant DE-FG02-02-92ER20075, and therefore the government may have certain rights to the invention.

This application is a divisional of U.S. application Ser. No. 10/555,795, filed Nov. 22, 2006, now abandoned, which is a 371 of PCT/US2004/014393, filed May 7, 2004, which claims the benefit of U.S. Provisional Application No. 60/468,966, filed May 8, 2003.

FIELD OF THE INVENTION

The present invention generally relates to a modified Rubisco large subunit $\epsilon$N-Methyltransferase (Rubisco LSMT, or RLSMT). The modified RLSMT is useful for targeting molecules to Rubisco. The present invention also relates to a modified RLSMT-carbonic anhydrase (RLSMT-CA). This modified RLSMT-CA improves the efficiency of the reduction of CO2 during photosynthesis, which may increase plant growth rates. The present invention also relates to nucleic acids encoding the modified RLSMT-CA or modified CA. Also, the present invention relates to cells including the modified RLSMT-CA or modified CA, plants containing the modified RLSMT-CA or modified RLSMT, and methods using compositions of the present invention. In addition, the present invention relates to antibodies conjugated to CA which may bind to the large or small subunits of Rubisco. The present invention provides methods of altering Rubisco carboxylase activity and altering plant growth.

BACKGROUND

Ribulose-1,5-bisphosphate carboxylase-oxygenase (Rubisco) catalyzes the reduction of atmospheric $CO_2$ during photosynthesis. This process is not efficient and methods to improve the efficiency of $CO_2$ reduction are needed. Methods which improve the efficiency of $CO_2$ reduction will increase plant growth rates, which will be useful to a variety of industries.

A great deal is known about the quaternary structure, catalytic mechanism, active site residues, in vivo regulatory mechanisms, and gene expression for this abundant enzyme, (see, for example, Andrews et al., "Rubisco: Structure, Mechanisms, and Prospects for Improvement," in Hatch et al. (eds), The Biochemistry of Plants, vol, 10, pp. 131-218. Academic Press, York (1987); Dean et al., "Structure, evolution, and regulation of rbcS genes in higher plants," Annu. Rev. Plant Physiol. Plant Mol. Biol. 40: 415-439 (1989); and Mullet, "Chloroplast development and gene expression," Annu. Rev. Plant. Physiol. Plant Mol. Biol. 39: 475-502 (1988)). Higher plant Rubisco is a hexadecameric protein composed of eight chloroplast-encoded large subunits (referred to herein as "LS") and eight nuclear-encoded small subunits (referred to herein as "SS"). Synthesis of the LS is accompanied by post-translational processing of the N-terminal domain (Houtz et al., "Post-translational modifications in the large subunit of ribulose bisphosphate carboxylase/oxygenase," Proc. Natl. Acad. Sci. USA 86:1855-1859 (1989); and Mulligan et al., "Reaction-intermediate analogue binding by ribulose bisphosphate carboxylase/oxygenase causes specific changes in proteolytic sensitivity: The amino-terminal residue of the large subunit is acetylated proline," Proc. Natl. Acad. Sci. USA 85:1513-1517 (1988)). The N-terminal Met-1 and Ser-2 are removed and Pro-3 acetylated. Additionally, the LS of Rubisco from tobacco, muskmelon, pea, and several other species is post-translationally modified by trimethylation of the $\epsilon$-amine of Lys-14 (Houtz et al., "Posttranslational modifications in the amino-terminal region of the large subunit of ribulose-1,5-bisphosphate carboxylase/oxygenase from several plant species," Plant Physiol. 98:1170-1174 (1992); Houtz et al., "Post-translational modifications in the large subunit of ribulose bisphosphate carboxylase/oxygenase," Proc. Natl. Acad. Sci. USA 86:1855-1859 (1989)). The enzyme responsible for this latter modification is a highly specific chloroplast-localized S-adenosylmethionine (AdoMet):protein (lys) $\epsilon$N-methyltransferase (protein methylase III, Rubisco LSMT, EC 2.1.1.43) (Houtz et al., "Post-translational modifications in the large subunit of ribulose bisphosphate carboxylase/oxygenase," Proc. Natl. Acad. Sci. USA 86:1855-1859 (1989)).

Rubisco LSMT has been affinity purified-8000-fold from pea chloroplasts and identified as a monomeric protein with a molecular mass of ~57 kDa (Wang et al., "Affinity Purification of Ribulose-1,5-bisphosphate Carboxylase/Oxygenase Large Subunit $\epsilon$N-Methyltransferase," Protein Expression and Purification 6:528-536 (1995)). Recently, Rubisco LSMT cDNAs have been cloned and sequenced from pea and tobacco (Klein et al., "Cloning and developmental expression of pea ribulose-1,5-bisphosphate carboxylase/oxygenase large subunit N-methyltransferase," Plant Molecular Biol. 27:249-261 (1995); Ying et a I., "Organization and characterization of the ribulose-1,5-bisphosphate carboxylase/oxygenase large subunit $\epsilon$N-methyltransferase gene in tobacco," Plant Molecular Biology 32:663-671 (1996)). The deduced amino acid sequences of tobacco Rubisco LSMT has 64.5% identity and 75.3% similarity with the sequence of pea Rubisco LSMT, and both proteins contain several copies of a conserved imperfect leucine-rich repeat motifs (Ying et al., "Organization and characterization of the ribulose-1,5-bisphosphate carboxylase/oxygenase large subunit $\epsilon$N-methyltransferase gene in tobacco," Plant Molecular Biology 32:663-671 (1996)).

Kaplan et al., in U.S. Pat. No. 6,320,101, addressed the need for increased efficiency of Rubisco $CO_2$ reduction by over-expressing a gene in a cell. However, the efficiency of $CO_2$ reduction in this method is not optimal and there is a need for additional methods of altering Rubisco carboxylase activity. There is a need for improved methods of targeting molecules to Rubisco.

SUMMARY

The present invention relates to a modified Rubisco large subunit $\epsilon$N-Methyltransferase (RLSMT). The modified RLSMT may include a Rubisco large subunit or biologically active fragment thereof linked to a second molecule or biologically active fragment thereof. The modified RLSMT may have the ability to bind a Rubisco.

In a further embodiment, upon binding of the modified RLSMT to Rubisco, the concentration of the second molecule is increased at the active site of Rubisco. Upon binding of the modified RLSMT to Rubisco, the concentration of another molecule may be increased at the active site of Rubisco. The second molecule may be carbonic anhydrase. The second molecule may be a phosphatase. The second molecule may be a 3-phosphoglycerate kinase, glyceraldehydes-3-phosphate dehydrogenase, Rubisco Activase, Phosphoribulokinase, polylysine, or oxygenase, for example. The another molecule may be $CO_2$. The second molecule may alter Rubisco activity. The another molecule may alter Rubisco activity.

The present invention relates to the polypeptide sequences of modified RLSMTs, the nucleic acid sequences encoding modified RLSMTs, expression vectors including the nucleic acid sequence encoding a modified RLSMT operably linked to an expression control sequence, host cells expressing one or more modified RLSMTs of the present invention, and plants and photosynthetic organisms containing host cells expressing one or more modified RLSMTs of the present invention. The growth of the plant containing the host cell may be altered.

Aspects of the present invention relate to methods of increasing the efficiency of $CO_2$ reduction in a cell. This increased efficiency of $CO_2$ reduction will result in increased plant productivity.

An embodiment of the present invention is a modified Rubisco large subunit $\epsilon$N-Methyltransferase-carbonic anhydrase (RLSMT-CA). The modified RLSMT-CA of the present invention may be linked to a carbonic anhydrase (CA). The modified RLSMT-CA may have the ability to bind a Rubisco. The carboxylase activity of Rubisco may be altered upon binding of Rubisco to the modified RLSMT-CA.

The present invention relates to the polypeptide sequences of modified RLSMT-CAs, the nucleic acid sequences encoding modified RLSMT-CAs, expression vectors including the nucleic acid sequence encoding a modified RLSMT-CA operably linked to an expression control sequence, host cells expressing one or more modified RLSMT-CAs of the present invention, and plants and photosynthetic organisms containing host cells expressing one or more modified RLSMT-CAs of the present invention. The growth of the plant containing the host cell may be altered.

The modified RLSMT-CAs of the present invention include Rubisco large subunit $\epsilon$N-Methyltransferase(s), which have been linked to CA by a chemical. The modified RLSMT-CAs of the present invention also include fusion proteins. The fusion proteins are encoded by a nucleic acid. The nucleic acid may include a first nucleic acid encoding a Rubisco large subunit $\epsilon$N-Methyltransferase or biologically active fragment thereof. The nucleic acid may further include a second nucleic acid encoding a carbonic anhydrase or biologically active fragment thereof. The order of these sequences may be reversed.

In a further embodiment, the modified RLSMT-CA may include an antibody or biologically active fragment thereof. The antibody may be linked to a CA or a biologically active fragment thereof.

The present invention further relates to an antibody which binds to a Rubisco large subunit $\epsilon$N-Methyltransferase. The antibody may be linked to or bind another molecule. The other molecule may be carbonic anhydrase. The Rubisco carboxylase activity may be altered upon binding of Rubisco to the RLSMT linked or bound to the antibody linked to or bound to the carbonic anhydrase.

The present invention further relates to a modified Rubisco subunit linked to a carbonic anhydrase (RSCA). The Rubisco subunit may be a Rubisco large subunit (LS) or a Rubisco small subunit (SS). The modified Rubisco subunit may assemble into Rubisco.

In a further embodiment, upon assembly of the modified LS or SS into Rubisco, the concentration of a first molecule is increased at the active site of Rubisco. Upon assembly of the modified LS and/or SS into Rubisco, the concentration of a second molecule may be increased at the active sites of Rubisco. The first molecule may be carbonic anhydrase. The second molecule may be $CO_2$. The first or second molecule may alter Rubisco activity.

The present invention relates to the polypeptide sequences of modified RSCA, the nucleic acid sequences encoding modified RSCA, expression vectors including the nucleic acid sequences encoding modified RSCA operably linked to an expression control sequence, host cells expressing one or more modified RSCAs of the present invention, and plants and photosynthetic organisms containing host cells expressing one or more modified RSCA of the present invention. The growth of the plant containing the host cell may be altered.

The present invention further relates to an antibody which binds to the LS or SS of Rubisco. The antibody may be linked to or bind another molecule. The other molecule may be carbonic anhydrase. The Rubisco carboxylase activity may be altered upon binding of the antibody linked to or bound to the carbonic anhydrase.

A method of altering Rubisco carboxylase activity is provided including providing a modified RLSMT-CA, modified RSCA, modified LSMT, a nucleic acid encoding a modified RLSMT-CA, modified RSCA, modified LSMT, or an antibody conjugated to CA.

A method of altering plant growth is provided including providing a modified RLSMT-CA, modified RSCA, modified LSMT, a nucleic acid encoding a modified RLSMT-CA, modified RSCA, modified LSMT, or an antibody conjugated to CA.

A particular embodiment is related to a method of delivering a molecule to the Rubisco active site. A Rubisco large subunit or small subunit is provided. A RLSMT is provided, which binds the Rubisco large or small subunit, wherein the Rubisco large and small subunits are integral components of Rubisco. The molecule to be delivered is bound to the RLSMT.

BRIEF DESCRIPTION OF DRAWINGS

The objects and advantages of the invention will be understood by reading the following detailed description in conjunction with the drawings in which:

FIG. 6A is the nucleic acid sequence of the RLSMT-CA (SEQ ID No.: 1). FIG. 6B is the amino acid sequence of the RLSMT-CA fusion protein (SEQ ID No.: 2).

DETAILED DESCRIPTION OF THE PREFERRED EMBODIMENTS

Unless otherwise stated, the following terms used in the specification and claims have the meanings given below:

By "RLSMT" is meant a Rubisco large subunit $\epsilon$N-Methyltransferase.

By "RLSMT-CA" is meant a Rubisco large subunit $^\epsilon$N-Methyltransferase-carbonic anhydrase.

By "RSCA" is meant a Rubisco subunit-carbonic anhydrase.

By "modified RLSMT-CA" is meant contains modifications or molecules not found in the wild-type RLSMT or wild-type CA.

By "Biologically active fragment" of a carbonic anhydrase is meant a polypeptide fragment of a carbonic anhydrase which has the ability to facilitate the equilibrium between dissolved $HCO_3$— and $CO_2$.

By "Biologically active fragment" of Rubisco large subunit $^\epsilon$N-Methyltransferase is meant a polypeptide fragment of a Rubisco large subunit $^\epsilon$N-Methyltransferase which has the ability to bind to Rubisco.

By a "vector" is meant a replicon, such as a plasmid, phage or cosmid, to which another DNA segment may be attached so as to bring about the replication of the attached segment.

General Description of the Present Invention

The present invention relates to the delivery of compounds and enzymes to the active-site vicinity of Rubisco. The presence and/or increased concentration of compounds and enzymes near the active-site vicinity of Rubisco may result in an increase in the carboxylase activity or specificity factor of Rubisco, for example. Increased carboxylase activity and specificity factor result in increased biomass production and thus translate into increased food and fiber production.

As described herein, localization of CA to Rubisco substantially increases the efficiency of $CO_2$ fixation by Rubisco at low $CO_2$. The delivery of enzymes such as Rubisco Activase may increase the efficacy of Rubisco Activase activity, an enzyme known to be essential for Rubisco activity. Also, the delivery of phosphatases specific for degradation of carboxyarabinitol-1-phosphate would also be useful since this compound is a known natural inhibitor of Rubisco activity that occurs in many plants. Furthermore the rapid metabolism of 3-phosphoglyceric acid, the immediate product of the carboxylase reaction, or 2-phosphoglycolate the immediate product of the oxygenase reaction, by targeting enzymes capable of metabolizing these products may also facilitate higher carboxylase activity or increases in the specificity factor of Rubisco. Other polypeptides such as polylysine and other amino acid polymers may also be beneficial by delivering additional carbon dioxide to Rubisco sequestered as carbamates on the amino acid amine groups.

Figure 1:
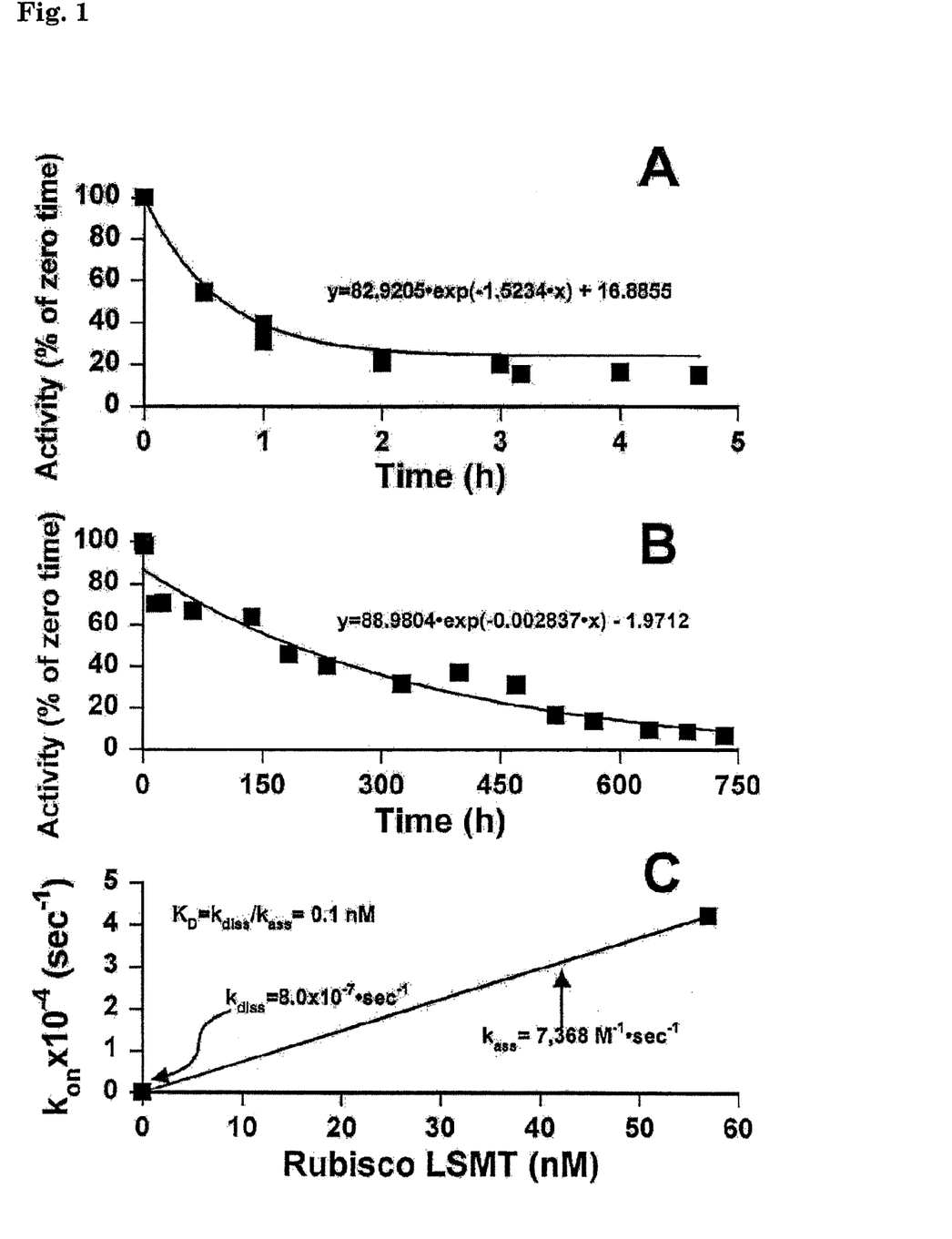
FIGS. 1A-C illustrate an estimation of the binding affinity of wild-type pea Rubisco LSMT for PVDF-immobilized des(methyl) spinach Rubisco.

The interaction between pea Rubisco LSMT and des(methyl) forms of Rubisco is exceptionally tight and specific (see FIG. 1). The interaction in general at least involves regions from the carboxy-terminal region of the LS of Rubisco and the amino-terminal region of pea Rubisco LSMT as measured by the susceptibility of Cys-119 and Cys-188 in pea Rubisco LSMT and Cys459 in the LS of spinach Rubisco to cross-linking by 1,6 Bismaleimidohexane (BMH, a homobifunctional sulfhydryl-specific cross-linking reagent). The interaction between pea Rubisco LSMT and des(methyl)spinach Rubisco appears to be stoichiometric with 1-4 monomers of pea Rubisco LSMT binding to each Rubisco holoenzyme. However, the binding has synergistic characteristics with decreasing binding affinity with increasing number of bound pea Rubisco LSMT monomers. Other regions of Rubisco LS and/or Rubisco SS may also be involved in Rubisco LSMT binding.

Given the tight binding of Rubisco LSMT to Rubisco, the present invention utilizes the Rubisco LSMT to deliver molecules to the active-site vicinity of Rubisco. A number of molecules may be delivered to Rubisco in this fashion. This provides utility for increasing the local concentration of a molecule at the active-site vicinity of Rubisco.

Modified Rubisco Large Subunit $^\epsilon$N-methyltransferase

A particular embodiment of the present invention relates to a modified Rubisco large subunit $^\epsilon$N-methyltransferase (RLSMT). The modified RLSMT contains a Rubisco large subunit $^\epsilon$N-methyltransferase or biologically active fragment thereof linked to a second molecule or biologically active fragment thereof. The modified RLSMT has the ability to bind to Rubisco. The modified RLSMT may result in an increase in the concentration of the second molecule near Rubisco. The second molecule may be carbonic anhydrase, a phosphatase, a 3-phosphoglycerate kinase, glyceraldehydes-3-phosphate dehydrogenase, Rubisco Activase, Phosphoribulokinase, polylysine, or oxygenase, for example. The increased concentration of the second molecule may increase the concentration of another molecule, such as $CO_2$ for example, near Rubisco. For example, the another molecule may be an enzymatic product of the second molecule. For example, the another molecule may be a molecule that binds the second molecule.

In a particular embodiment, the Rubisco large subunit $^\epsilon$N-methyltransferase is linked to the second molecule by a chemical. Representative chemicals useful for linking these molecules are well-known to one of skill in the art. In this example the linkage is through free amine groups using glutaraldehyde. The use of any reactive molecule capable of cross-linking two proteins is also contemplated in this embodiment. Non-limiting examples of such cross-linking reagents are APG—(p-Azidophenyl gloxal monohydrate)—specific for arginine residues, BMH—(Bismaleimidohexane)—specific for sulfhydryl groups, DSP (Lomant's Reagent)—(Dithiobis[succinimidylpropionate])—specific for amines, EGS—(Ethylene glycolbis-[succinimidylsuccinate])—specific for amines, EDC—(1-Ethyl-3-[3-dimethylaminopropyl]-carboiimide Hydrochloride)—specific for amines and carboxyls, MBS—(m-Maleimidobenzoyl-N-hydroxysuccinimide ester)—specific for sulfhydryls and amines, HPG—(p-Hydroxyphenylglyoxal)—specific for argine residues, SPDP—(N-Succinimidyl-3-[2-pyridyldithio]propioinate)—reactive with amines and sulhydryls, Sulfo-SAPB—(Sulfosuccinimidyl 4-[p-azidophenyl]butyrate)—amines and photoreactive, and BSOCOES—(Bis[2-(succinimidooxycarbonyloxy)ethyl]sulfone)—reactive with amines.

In a particular embodiment, the modified RLSMT is a fusion protein. The fusion protein may be encoded by a nucleic acid sequence, wherein the nucleic acid sequence comprises a first nucleic acid sequence encoding a Rubisco large subunit $^\epsilon$N-methyltransferase or biologically active fragment thereof, and wherein the nucleic acid sequence further comprises a second nucleic acid sequence encoding a polypeptide. Methods of molecular biology useful in these methods are well-known to one of skill in the art. In a particular embodiment, the second nucleic acid encodes carbonic anhydrase. In a particular embodiment, the second nucleic acid encodes a phosphatase. The second nucleic acid may encode a 3-phosphoglycerate kinase, glyceraldehydes-3-phosphate dehydrogenase, Rubisco Activase, Phosphoribulokinase, polylysine, or oxygenase, for example. The order of these sequences may be reversed.

A particular embodiment of the present invention relates to a modified Rubisco large subunit. The modified RLS contains a Rubisco large subunit or biologically active fragment thereof linked to a second molecule or biologically active fragment thereof.

In a particular embodiment, the Rubisco large subunit is linked to the second molecule by a chemical. Representative chemicals useful for linking these molecules are well-known to one of skill in the art.

In a particular embodiment, the modified Rubisco large subunit is a fusion protein. The fusion protein may be encoded by a nucleic acid sequence, wherein the nucleic acid sequence comprises a first nucleic acid sequence encoding a Rubisco large subunit or biologically active fragment thereof, and wherein the nucleic acid sequence further comprises a second nucleic acid sequence encoding a polypeptide. Methods of molecular biology useful in these methods are well-known to one of skill in the art. In a particular embodiment, the second nucleic acid encodes carbonic anhydrase. The order of these sequences may be reversed.

A particular embodiment of the present invention relates to a modified Rubisco small subunit. The modified RSS contains a Rubisco small subunit or biologically active fragment thereof linked to a first molecule or biologically active fragment thereof.

In a particular embodiment, the Rubisco small subunit is linked to the second molecule by a chemical. Representative chemicals useful for linking these molecules are well-known to one of skill in the art.

In a particular embodiment, the modified Rubisco small subunit is a fusion protein. The fusion protein may be encoded by a nucleic acid sequence, wherein the nucleic acid sequence comprises a first nucleic acid sequence encoding a Rubisco small subunit or biologically active fragment thereof, and wherein the nucleic acid sequence further comprises a second nucleic acid sequence encoding a polypeptide. Methods of molecular biology useful in these methods are well-known to one of skill in the art. In a particular embodiment, the second nucleic acid sequence encodes carbonic anhydrase. The order of these sequences may be reversed.

A particular embodiment of the present invention relates to a modified carbonic anhydrase. The modified carbonic anhydrase contains a carbonic anhydrase or biologically active fragment thereof linked to a first molecule or biologically active fragment thereof.

In a particular embodiment, the carbonic anhydrase is linked to the second molecule by a chemical. Representative chemicals useful for linking these molecules are well-known to one of skill in the art.

In a particular embodiment, the modified carbonic anhydrase is a fusion protein. The fusion protein may be encoded by a nucleic acid sequence, wherein the nucleic acid sequence comprises a first nucleic acid sequence encoding a carbonic anhydrase or biologically active fragment thereof, and wherein the nucleic acid sequence further comprises a second nucleic acid sequence encoding a polypeptide. Methods of molecular biology useful in these methods are well-known to one of skill in the art. The order of these sequences may be reversed. Preferably, the second molecule is RLSMT, Rubisco LS, Rubisco SS, or a protein that binds either Rubisco LS or Rubisco SS. The second molecule may be Rubisco LSMT. Most preferably, the carboxylase activity of Rubisco is altered upon binding of the modified carbonic anhydrase to Rubisco LS or Rubisco SS.

In accordance with the present invention there may be employed conventional molecular biology, microbiology, immunology, and recombinant DNA techniques within the skill of the art. Such techniques are explained fully in the literature. See, e.g., Sambrook et al, "Molecular Cloning: A Laboratory Manual" (3$^{rd}$ edition, 2001); "Current Protocols in Molecular Biology" Volumes I-IV [Ausubel, R. M., ed. (2002 and updated bimonthly)]; "Cell Biology: A Laboratory Handbook" Volumes I-III [J. E. Celis, ed. (1994)]; "Current Protocols in Immunology" Volumes I-IV [Coligan, J. E., ed. (2002 and updated bimonthly)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Culture of Animal Cells, 4$^{th}$ edition" [R. I. Freshney, ed. (2000)]; "Immobilized Cells And Enzymes" [IRL Press, (1986)]; B. Perbal, "A Practical Guide To Molecular Cloning" (1988); *Using Antibodies: A Laboratory Manual: Portable Protocol No. I*, Harlow, Ed and Lane, David (Cold Spring Harbor Press, 1998); *Using Antibodies: A Laboratory Manual*, Harlow, Ed and Lane, David (Cold Spring Harbor Press, 1999).

Rubisco large subunit $\epsilon$N-methyltransferases useful in the present invention may be derived from any plant or photosynthetic organism.

Upon binding of the modified RLSMT to Rubisco, the concentration of the first molecule may be increased at the active site of Rubisco. The first molecule may be carbonic anhydrase or biologically active fragments thereof. The first molecule may alter Rubisco activity.

Upon binding of the modified RLSMT to Rubisco, the concentration of a second molecule may be increased at the active site of Rubisco. The second molecule may be the product of a reaction catalyzed by the first molecule. The second molecule may be $CO_2$. The second molecule may alter Rubisco activity.

In a particular embodiment, the modified Rubisco large subunit $\epsilon$N-methyltransferase is in a complex with carbonic anhydrase. The modified Rubisco large subunit $\epsilon$N-methyltransferase may be linked to carbonic anhydrase or a biologically active fragment thereof. The modified RLSMT-CA has the ability to bind Rubisco. Rubisco activity is altered when bound to the RLSMT-CA complex.

In a particular embodiment, the Rubisco large subunit $\epsilon$N-methyltransferase is linked to the carbonic anhydrase by a chemical. Representative chemicals useful for linking these molecules are well-known to one of skill in the art.

In a particular embodiment, the modified RLSMT-CA is a fusion protein. The fusion protein is encoded by a nucleic acid sequence, wherein the nucleic acid sequence includes a first nucleic acid sequence encoding a Rubisco large subunit $\epsilon$N-methyltransferase or biologically active fragment thereof, and wherein the nucleic acid sequence further includes a second nucleic acid sequence encoding a carbonic anhydrase or biologically active fragment thereof. The order of these sequences may be reversed.

In a particular embodiment, the Rubisco complex with carbonic anhydrase includes an antibody. The antibody may be linked to a carbonic anhydrase. Preferably, the antibody may bind to Rubisco LS or Rubisco SS.

In a particular embodiment, the Rubisco large subunit $\epsilon$N-methyltransferase-CA complex is within a cell. The cell may be prokaryotic or eukaryotic. The cell may be a plant cell or plant tissue.

In a particular embodiment, the Rubisco large subunit $\epsilon$N-methyltransferase-CA complex is in a photosynthetic organism.

Rubisco Large Subunit $\epsilon$N-methyltransferase Carbonic Anhydrase

An aspect of the present invention addresses the need to increase the rate of $CO_2$ fixation by Rubisco, which is an inefficient process in wild-type plants. An increased rate of $CO_2$ fixation by Rubisco will increase plant productivity, which is useful in terms of food, fiber, and biomass and is applicable to various aspects of agriculture.

At atmospheric levels of $CO_2$, the carboxylase activity of Rubisco is limited. Additional limitations occur as a consequence of competitive inhibition by $O_2$. However, many plants possess mechanisms to alleviate this constraint, and increase the rate of $CO_2$ fixation by compartmentalization of Rubisco in conjunction with accumulation of inorganic carbon or $CO_2$. An important part of this mechanism is carbonic anhydrase that facilitates equilibrium between dissolved $HCO_3-$ and $CO_2$. Given the tight and specific binding of Rubisco LSMT to des(methyl) forms of Rubisco, and the absence of any negative consequences from this binding on the catalytic activity of Rubisco, studies were undertaken to target carbonic anhydrase (CA) to Rubisco utilizing Rubisco LSMT. The results from these experiments demonstrate that localization of CA to Rubisco substantially increases the efficiency of $CO_2$ fixation by Rubisco at low $CO_2$.

A particular embodiment of the present invention relates to a modified Rubisco large subunit $^\epsilon$N-methyltransferase-carbonic anhydrase (RLSMT-CA) complex, wherein the Rubisco large subunit $^\epsilon$N-methyltransferase is linked to carbonic anhydrase. This RLSMT-CA complex has the ability to bind to Rubisco, and Rubisco carboxylase activity is altered when bound to the RLSMT-CA complex.

The reduction in the apparent affinity for $CO_2$ by the direct placement of CA to the active-site vicinity of Rubisco circumvents the kinetic constraints and enables Rubisco to maintain nearly saturated rates of carboxylase activity at air levels of $CO_2$.

Methods of the Present Invention

A method of altering Rubisco carboxylase activity is provided including modifying CA by providing a modified RLSMT-CA, a nucleic acid sequence encoding a RLSMT-CA, or an antibody conjugated to CA.

A method of altering plant growth is provided including modifying the RLSMT-CA by providing a modified RLSMT-CA, a nucleic acid sequence encoding a RLSMT-CA, or an antibody conjugated to CA.

A particular embodiment is related to a method of delivering a molecule to the vicinity of the Rubisco active site. A Rubisco large or small subunit is provided. A RLSMT is provided, which binds the Rubisco large or small subunit. The molecule to be delivered is bound to the RLSMT.

Antibody

Also, antibodies including both polyclonal and monoclonal antibodies, and drugs that modulate the production or activity of the modified RLSMT-CAs, modified RLSMTs, Rubisco LSs, Rubisco SSs, and/or their biologically active fragments or subunits may be useful in the production or modification of modified RLSMT-CAs, modified RLSMTs, Rubisco LSs, or Rubisco SSs. Antibodies may be conjugated to another molecule, such as a carbonic anhydrase. For example, RLSMT-CAs, modified RLSMTs, Rubisco LSs, Rubisco SSs, or fragments or subunits thereof may be used to produce both polyclonal and monoclonal antibodies, to the RLSMT-CAs, modified RLSMTs, Rubisco LSs, Rubisco SSs, or fragments or subunits thereof, in a variety of cellular media, by known techniques such as the hybridoma technique utilizing, for example, fused mouse spleen lymphocytes and myeloma cells. Likewise, small molecules that mimic or antagonize the activity(ies) of the RLSMT-CAs, modified RLSMTs, Rubisco LSs, or Rubisco SSs, of the invention may be discovered or synthesized, and may be used in diagnostic and/or therapeutic protocols.

The present invention also extends to the development of antibodies against the modified RLSMT-CAs, modified RLSMTs, Rubisco LSs, Rubisco SSs, including naturally raised and recombinantly prepared antibodies. For example, the antibodies could be used to modulate Rubisco activity, or in the production or modulation of a modified RLSMT-CA or modified RLSMT.

The general methodology for making monoclonal antibodies by hybridomas is well known. Methods for producing monoclonal anti-modified RLSMT-CA, modified RLSMT, Rubisco LS, Rubisco SS, or Rubisco antibodies are also well-known in the art. See Niman et al., *Proc. Natl. Acad. Sci. USA*, 80:4949-4953 (1983). Typically, the modified RLSMT-CA, modified RLSMT, Rubisco LS, Rubisco SS, Rubisco or a peptide analog is used either alone or conjugated to an immunogenic carrier, as the immunogen in the before described procedure for producing anti-modified RLSMT-CA, modified RLSMT, Rubisco LS, Rubisco SS, or Rubisco monoclonal antibodies. The culture is maintained under conditions and for a time period sufficient for the hybridoma to secrete the antibodies into the medium. The hybridomas are screened for the ability to produce an antibody that immunoreacts with the modified RLSMT-CA, modified RLSMT, Rubisco LS, Rubisco SS, Rubisco or peptide analog. The antibody-containing medium is then collected. The antibody can then be further isolated by well-known techniques. Immortal, antibody-producing cell lines can also be created by techniques other than fusion, such as direct transformation of B lymphocytes with oncogenic DNA, or transfection with Epstein-Barr virus. See, e.g., Using Antibodies: A Laboratory Manual, Harlow, Ed and Lane, David (Cold Spring Harbor Press, 1999).

Media useful for the preparation of these compositions are both well-known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/l glucose, 20 mm glutamine, and 20% fetal calf serum. A preferred inbred mouse strain is the Balb/c.

Methods for producing polyclonal anti-polypeptide antibodies are well-known in the art. See U.S. Pat. No. 4,493,795 to Nestor et al. A monoclonal antibody, and immunologically active fragments thereof, can be prepared using the hybridoma technology described in e.g., Using Antibodies: A Laboratory Manual, Harlow, Ed and Lane, David (Cold Spring Harbor Press, 1999), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a modified RLSMT-CA, modified RLSMT, Rubisco LS, Rubisco SS, or Rubisco. Splenocytes are typically fused with myeloma cells using polyethylene glycol (PEG) 6000 MW. Fused hybrids are selected by their sensitivity to HAT (hypoxanthine, aminopterin, thymidine) supplemented media. Hybridomas producing a monoclonal antibody useful in practicing this invention are identified by their ability to immunoreact with the present modified RLSMT-CA, modified RLSMT, Rubisco LS, Rubisco SS, or Rubisco and their ability to alter specified modified RLSMT-CA, modified RLSMT, Rubisco LS, Rubisco SS, or Rubisco activity in target cells.

Panels of monoclonal antibodies produced against modified RLSMT-CA, modified RLSMT, Rubisco LS, Rubisco SS, or Rubisco peptides can be screened for various properties, i.e., isotype, epitope, affinity, and the like. High affinity antibodies are also useful when immunoaffinity purification of native or recombinant modified RLSMT-CA, modified RLSMT, Rubisco LS, Rubisco SS, or Rubisco is possible.

Cells, Tissues, and Substrates

The cells of the present invention may express at least one modified Rubisco Large Subunit $\epsilon$N-methyltransferase. The cells may further comprise a conjugate of a carbonic anhydrase and Rubisco Large Subunit $\epsilon$N-methyltransferase. Useful cells include eukaryotic and prokaryotic cells, including, but not limited to, bacterial cells, yeast cells, fungal cells, insect cells, nematode cells, plant cells, and animal cells. Suitable animal cells include, but are not limited to, HEK-293 cells, U2OS cells, HeLa cells, COS cells, and various primary mammalian cells.

In a preferred embodiment of the present invention, the photosynthetic organism is a C3 plant. Non-limiting examples of C3 plants include spinach, wheat, rice, and barley.

The cells of the present invention may express one modified Rubisco large subunit $\epsilon$N-methyltransferase that results in enhanced carbon fixation upon expression in a plant.

A substrate may have deposited thereon a plurality of cells of the present invention. The substrate may be any suitable biologically substrate, including but not limited to, glass, plastic, ceramic, semiconductor, silica, fiber optic, diamond, biocompatible monomer, or biocompatible polymer materials.

Nucleic Acids Encoding Modified Rubisco

The present invention further includes nucleic acid molecules that encode modified Rubisco large subunit $\epsilon$N-methyltransferase. It should be appreciated that also within the scope of the present invention are DNA sequences encoding modified Rubisco large subunit $\epsilon$N-methyltransferase.

The modified Rubisco large subunit $\epsilon$N-methyltransferases may be generated by molecular biological techniques standard in the genetic engineering art, including but not limited to, polymerase chain reaction (PCR), restriction enzymes, expression vectors, plasmids, and the like. By way of example, vectors may be designed which contain a signal sequence. PCR amplified DNA fragments of a modified Rubisco large subunit $\epsilon$N-methyltransferase to be modified may be digested by appropriate restriction enzymes and subcloned into the vector. Modifications of the DNA may be introduced by standard molecular biological techniques as described above.

Transformation

In order to prepare the integration of foreign genes into higher plants a high number of cloning vectors are available, containing a replication signal for *E. coli* and a marker gene for the selection of transformed bacterial cells. Examples for such vectors include, but are not limited to, pBR322, pUC series, M13 mp series, pACYC184. The desired sequence may be integrated into the vector at a suitable restriction site. The obtained plasmid is used for the transformation of *E. coli* cells. Transformed *E. coli* cells are cultivated in a suitable medium end subsequently harvested and lysed. The plasmid is recovered. Restriction analysis, gel electrophoresis and other biochemico-molecular biological methods may be used to analyze the obtained plasmid DNA. After each manipulation the plasmid DNA may be cleaved and the obtained DNA fragments may be linked to other DNA sequences. Each plasmid DNA may be cloned into the same or into other plasmids.

In order to integrate DNA into plant host cells a wide range of techniques are available. These techniques comprise the transformation of plant cells with T-DNA by using *Agrobacterium tumefaciens* or *Agrobactedium rhizogenes* as transformation medium, the fusion of protoplasts, the injection and the electroporation of DNA, the integration of DNA by means of the biolistic method as well as further possibilities.

Several modes of delivery of the DNA are know to those of skill in the art. For example, DNA may be delivered into the nuclear genome, or the chloroplast genome. If delivered into the nuclear genome, the construct will have to an N-terminal sequence included in the construct capable of targeting the fusion to the chloroplast. This technique well known to one of skill in the art, may use the transit sequence for the SS of Rubisco, which is known to be chloroplast-localized, but is a nuclear-encoded gene. Alternatively, recent advances also allow for delivery of the fusion construct directly into the chloroplast genome, which obviates the necessity for a chloroplast targeting sequence. These methods are described, for example, in Karlin, Neumann, G. A. and Tobin, E. M., EMBO J. 5 (1986) 9-13; Liu, Y. Y., Kaderbhai, N., and Kaderbhai, M. A., Biochem. J. 351 Pt 2 (10-15-2000) 377-384; Mishkind, M. L., Wessler, S. R., and Schmidt, G. W., J. Cell Biol. 100 (1985) 226-234; Huang, F. C., Klaus, S. M., Herz, S., Zou, Z., Koop, H. U., and Golds, T. J., Mol. Genet. Genomics 268 (2002) 19-27; Madoka, Y., Tomizawa, K., Mizoi, J., Nishida, I., Nagano, Y., and Sasaki, Y., Plant Cell Physiol 43 (2002) 1518-1525.

In the case of injection and electroporation of DNA into plant cells, plasmids such as pUC derivatives may be used. However, In cases in which whole plants are to be regenerated from transformed cells, a selectable marker gene should be present.

Depending on the method used for integrating desired genes into the plant cell, further DNA sequences such as Ti- and Ri-plasmid T-DNA may be necessary.

If *Agrobacteria* are used for the transformation, the DNA which is to be integrated must be cloned into special plasmids, namely either into an intermediate vector or into a binary vector. Due to sequences homologous to the sequences within the T-DNA, the intermediate vectors may be integrated into the Ti- or Ri-plasmid of the *Agrobacterium* due to homologous recombination. This also contains the vir-region necessary for the transfer of the T-DNA. Intermediate vectors cannot replicate in *Agrobacteria*. By means of a helper plasmid the intermediate vector may be transferred to *Agrobacterium tumefaciens* (conjugation). Binary vectors may replicate in *E. coli* as well as in *Agrobacteria*. They contain a selectable marker gene as well as a linker or polylinker which is framed by the right and the left T-DNA border region. They may be transformed directly into the *Agrobacteria* (Holsters et al. Mol. Gen. Genet. 163 (1978), 181-187). The *Agrobacterium* acting as host cell should contain a plasmid carrying a vir-region. The vir-region is necessary for the transfer of the T-DNA into the plant cell. Additional T-DNA may be present. The *Agrobacterium* transformed in such a way is used for the transformation of plant cells.

The use of T-DNA for the transformation of plant cells was investigated intensely and described in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1-46 and An et al. EMBO J. 4 (1985), 277-287.

For transferring the DNA into the plant cells, plant explants may suitably be co-cultivated with *Agrobacterium tumefaciens* or *Agrobacterium rhizogenes*. From the infected plant material (e.g. pieces of leaves, stem segments, roots, but also protoplasts or suspension-cultivated plant cells) whole plants may then be regenerated in a suitable medium which may contain antibiotics or biozides for the selection of transformed cells. The plants obtained in such a way may then be examined as to whether the integrated DNA is present or not. Other possibilities in order to integrate foreign DNA by using the biolistic method or by transforming protoplasts are known to the skilled person (cf., e.g., Willmitzer, L., 1993 Transgenic plants. In: Biotechnology, A Multi-Volume Comprehensive Treatise (H. J. Rehm, G. Reed, A. Puhler, P. Stadler, editors), Vol. 2, 627-659, VCH Weinheim-New York-Basel-Cambridge).

Once the introduced DNA has been integrated in the genome of the plant cell, it usually continues to be stable and also remains within the descendants of the originally transformed cell. It usually contains a selectable marker which confers resistance against a biozide or against an antibiotic such as kanamycin, G 418, bleomycin, hygromycin or phosphinotricine, etc. to the transformed plant cells. The individually selected marker should therefore allow for a selection of transformed cells to cells lacking the integrated DNA.

The transformed cells grow in the usual way within the plants (see also McCormick et al., 1986, Plant Cell Reports 5: 81-84).

The resulting plants can be cultivated in the usual way and cross-bred with plants having the same transformed genetic heritage or another genetic heritage. The resulting hybrid individuals have the corresponding phenotypic properties. Two or more generations should be grown in order to ensure whether the phenotypic feature is kept stably and whether it is transferred. Furthermore, seeds should be harvested in order to ensure that the corresponding phenotype or other properties will remain.

Although the present invention has been described in detail with reference to examples above, it is understood that various modifications can be made without departing from the spirit of the invention, and would be readily known to the skilled artisan. Additionally, the invention is not to be construed to be limited by the following examples.

EXAMPLES

Example 1

Materials and Methods

Spinach Rubisco was purified and stored according to McCurry, S. D., Gee, R., and Tolbert, N. E. *Methods Enzymol.* 90 Pt E, 515-521.1982. hCAII DNA was transformed into BL21 DE3 pLYS S and expressed, purified, and stored according to Tanhauser, S. M., Jewell, D. A., Tu, C. K., Silverman, D. N., and Laipis, P. J. Gene 117, 113-117.1992. hCAII was assayed according to Cronk, J. D., Endrizzi, J. A., Cronk, M. R., O'neill, J. W., and Zhang, K. Y. *Protein Sci.* 10, 911-922. 2001, Khalifah, R. G. *The Journal of Biological Chemistry* 246, 2561-2573. 1971 Wilbur, K. M. and Anderson, N. G. *The Journal of Biological Chemistry* 176, 147-154. 1948. Rubisco LSMT was expressed, purified, stored, and assayed according to Wang, P., Royer, M., and Houtz, R. L. *Protein Expr. Purif.* 6, 528-536. 1995.

Example 2

Binding of Rubisco LSMT and des(methyl) Forms of Rubisco

Figure 4:
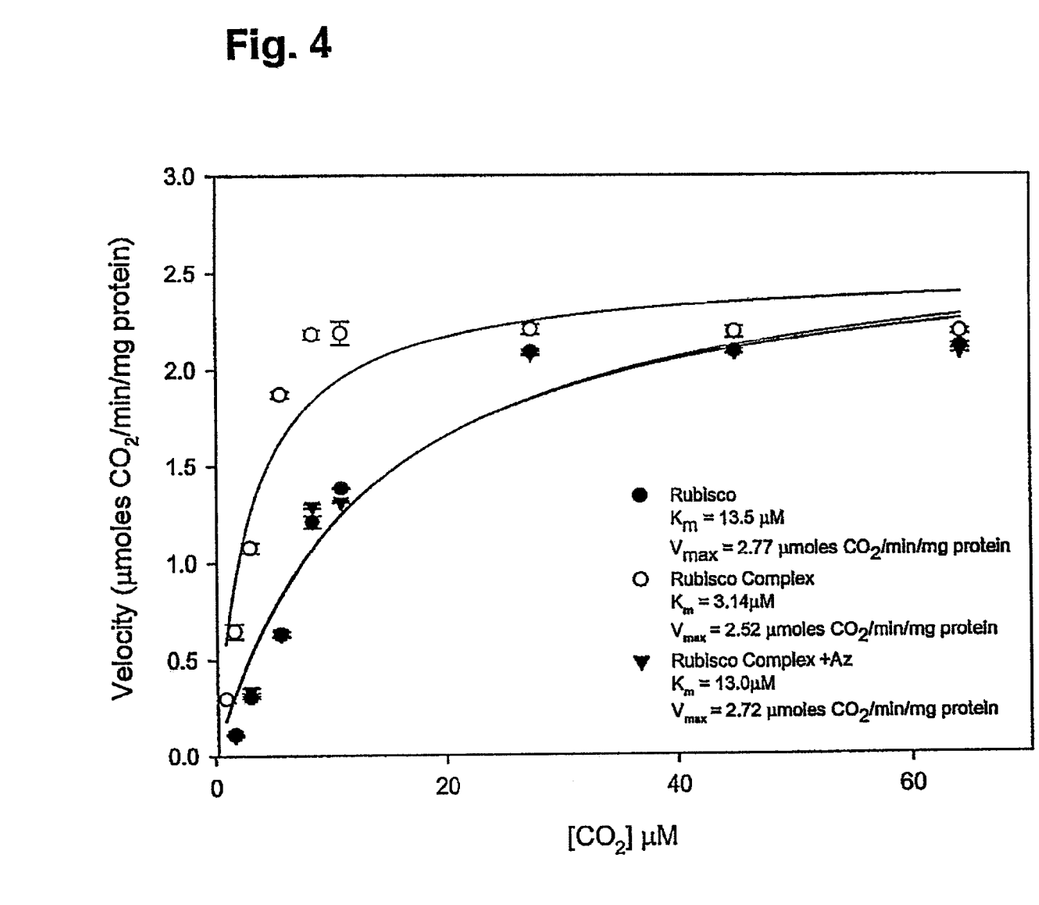
FIG. 4 illustrates kinetic analyses of Rubisco, Rubisco complexed with hCA, Rubisco complexed with hCA in the presence of acetazolamide (Az).

Purified Rubisco LSMT and hCAII (1:8 M ratio) reacted in buffer A with 0.5% glutaraldehyde for 2 hours at room temperature (approx. 22° C.). The glutaraldehyde was quenched by the addition of Tris to 0.4 M, then dialyzed exhaustively in the microdialyzer (MWCO 8000) against buffer B at 4° C. Conjugated protein was then incubated in buffer B with purified spinach Rubisco (1 Rubisco:2 conjugate molar ratio) for 4 hours on ice. The multienzyme complex (conjugate) was subjected to Sepharose CL 6B gel permeation chromatography (1×45 cm column) and resolved at 0.1 mL/min into 0.5 mL fractions. The Sepharose CL 6B column was calibrated according to manufacturer's instructions (FIG. 4). Fractions were analyzed for Rubisco LSMT, Rubisco, and hCAII activities as described above.

Figure 3:
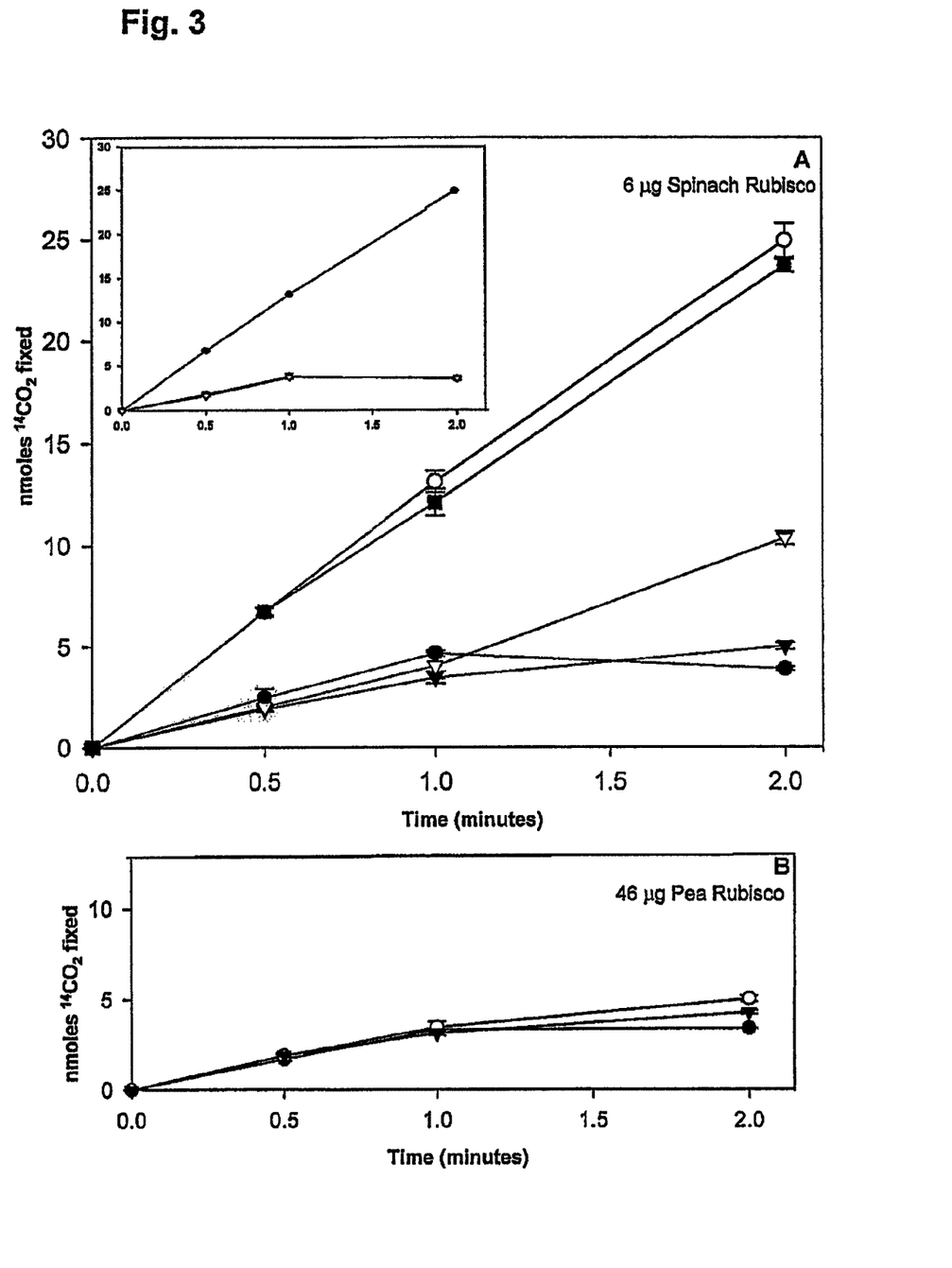
FIGS. 3A-B illustrate the effect of HCAII conjugated to Rubisco LSMT on carboxylase activity of spinach and pea Rubisco.

A human form of carbonic anhydrase (hCA) was chemically cross-linked with Rubisco large subunit (LS) $^\varepsilon$N-Methyltransferase (Rubisco LSMT). The complex between hCA and Rubisco LSMT retained the highly specific and tight-binding affinity (KD≅0.1 nM) for des(methyl) forms of Rubisco characteristic of Rubisco LSMT. Binding of this complex to Rubisco, and localization of carbonic anhydrase to the active-site vicinity of Rubisco, resulted in a significant increase in the carboxylation efficiency of Rubisco manifested as a decrease in the $K_m$ ($CO_2$) from 13.4 μM to 3.44 μM (FIG. 4). Since the level of dissolved $CO_2$ in equilibrium with air (~360 ppm) is approximately 15 μM, it has been widely recognized for decades that a major limitation to plant productivity and biomass production is the kinetic constraint for $CO_2$ fixation by Rubisco. At air levels of $CO_2$, the enzymatic velocity for carboxylation by Rubisco is only half of the potential velocity, and additionally is further reduced by competitive inhibition by oxygen. These two factors reduce the carboxylation efficiency of Rubisco, to the point that nearly all crop plants show a remarkable stimulation of growth and productivity when cultured under atmospheres enriched in $CO_2$. The reduction in the apparent affinity for $CO_2$ by the direct placement of CA to the active-site vicinity of Rubisco circumvents these kinetic constraints and enables Rubisco, to maintain nearly saturated rates of carboxylation at air levels of $CO_2$ (see FIG. 3, panel A and inset). It is contemplated in the present invention that these results can be duplicated using gene fusion techniques, and introduced into transgenic plants. The potential exists to increase plant productivity by 50-100% in all C3 plants (a form of biochemical plant classification based on photosynthesis that represents the majority of crop plants).

FIG. 1. Estimation of the binding affinity of wild-type pea Rubisco LSMT for PVDF-immobilized des(methyl) spinach Rubisco. FIG. 1A shows the loss in Rubisco LSMT activity at 4° C. from pea chloroplast lysates over time during incubation with PVDF-immobilized Rubisco. The concentration of Rubisco LSMT was estimated at 58 nM from activity measurements assuming a specific activity of purified pea Rubisco LSMT of 306 nmoles/min/mg protein. FIG. 1B shows the loss in bound Rubisco LSMT activity at 4° C. from PVDF-immobilized spinach Rubisco over time as determined by activity measurements of bound Rubisco LSMT. Immunological analyses confirmed that the loss in Rubisco LSMT activity was due to disassociation and not catalytic inactivation. FIG. 1C shows an affinity plot of data from FIG. 1A and FIG. 1B estimating the affinity constant KD for the binding of pea Rubisco LSMT to spinach Rubisco.

Example 3

Purification of Rubisco LSMT and des(methyl) Forms of Rubisco

Several studies have suggested that the activity of CA could be essential for optimum rates of photosynthetic $CO_2$ fixation in C3 plants at low levels of $CO_2$. Ample evidence exists for an essential role of CA in the CCM (carbon concentrating mechanism) in C4 plants, and aquatic species with CCMs. Other studies have identified an association of CA with Calvin cycle enzymes and photosystem II complexes, as well as more defined localizations to pyrenoids and carboxysomes. However, direct experimental evidence of whether or not a close association of CA with Rubisco results in increased rates of $CO_2$ fixation is unavailable. The possibility that CA placed in direct proximity to Rubisco influences the rate or extent of $CO_2$ fixation at low $CO_2$ by creating catalytically and binding competent conjugates between HCAII (human carbon anhydrase II) and pea Rubisco LSMT was explored in the present invention. This complex has a relatively large molecular mass, binds to des(methyl) spinach Rubisco, retains CA, Rubisco LSMT, and Rubisco activity, and is immunologically reactive with Rubisco LSMT antibody (FIGS. 2A, B, and D). The complex does not bind to pea Rubisco (FIG. 2A).

Figure 2:
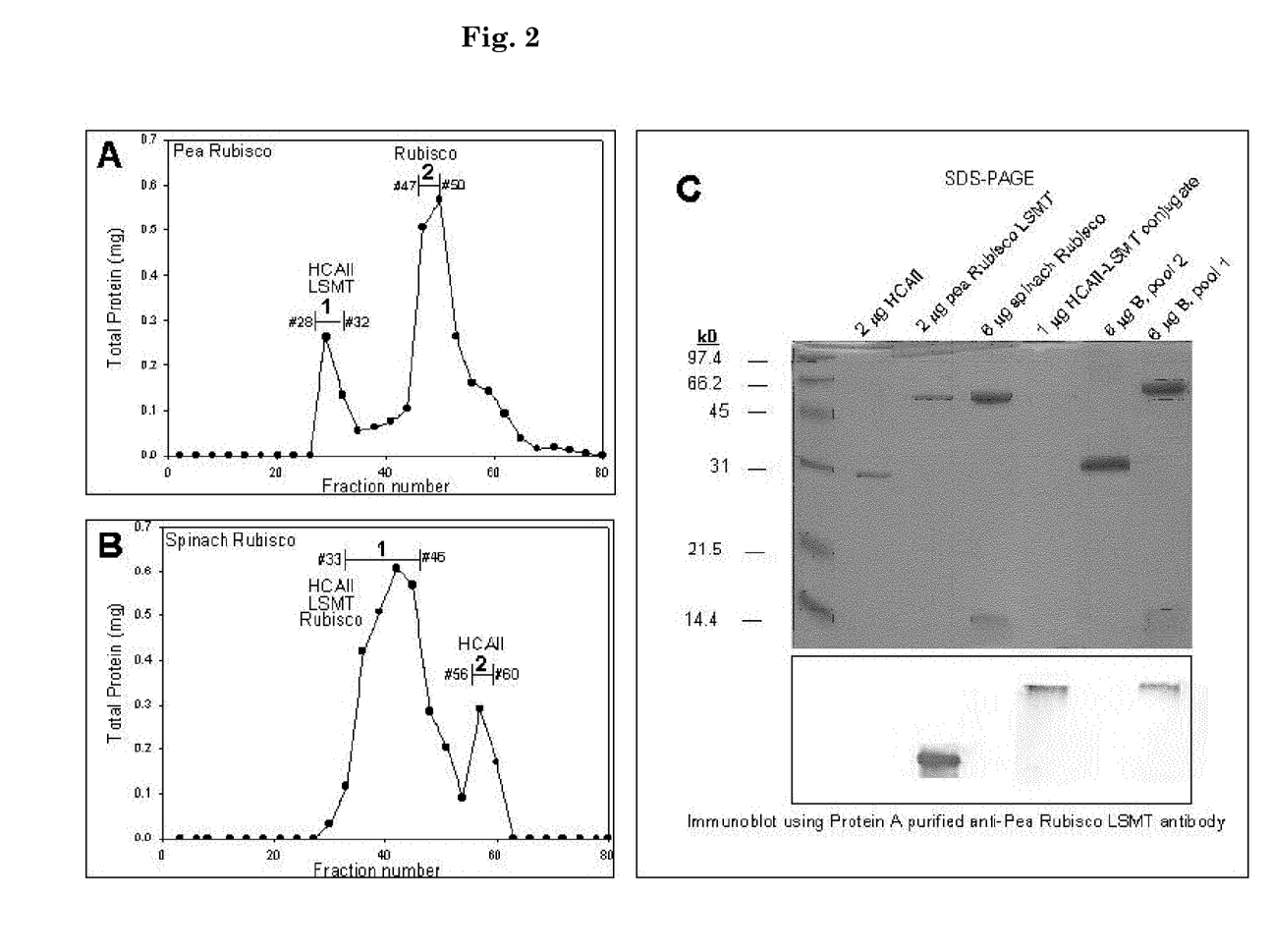
FIGS. 2A-C illustrate the fractionation of human carbonic anhydrase II (HCAII)-Rubisco LSMT conjugate, Rubisco, Rubisco LSMT, and HCAII by chromatography on Sepharose 6B.

FIG. 2. Fractionation of human carbonic anhydrase II (HCAII)-Rubisco LSMT conjugate, Rubisco, Rubisco LSMT, and HCAII by chromatography on Sepharose 6B. Human carbonic anhydrase II enzyme (HCAII), kindly provided by P. J. Laipis, was induced according to Tanhauser, et al., Gene 117: 113-117 (1992), purified according to Whitley, et al., Anal. Biochem. 57: 467-476 (1974), and assayed according to Cronk, et al., Protein Sci. 10: 911-922 (2001) (2.22 µmoles/min/ng protein, 3 Wilbur-Anderson (W-A) units/µg). Spinach and pea Rubisco, and pea Rubisco LSMT were purified according to McCurry, et al., Methods Enzymol. 90 Pt E: 515-521 (1982) and Zheng, et al., Protein Expr. Purif. 14:104-112 (1998) respectively. Pea Rubisco LSMT and HCAII were conjugated at a 1:8 molar ratio (240 µM:1.92 mM) in 0.1 M potassium phosphate buffer, pH 6.8, by incubation for 2 hours at 25° C. with (0.5% v/v) glutaraldehyde. Excess glutaraldehyde was quenched by the addition of Tris buffer, pH 8.2, to 0.4 M and the reaction dialyzed exhaustively against 50 mM Bicine, pH 8.2. The conjugated reaction products were incubated with 10 mg of pea (A) or spinach (B) Rubisco for 2 hours at 25° C. The solution (0.5 mL) was applied to a Sepharose 6B gel permeation column (1.5×45 cm) and eluted at 0.1 mL/min in 50 mM Bicine pH 8.2. Protein concentration was determined by the Bradford method. Pooled fractions were enzymatically assayed for HCAII according to Cronk, et al., Protein Sci. 10: 911-922 (2001) (A, pool 1, 1.69 W-A; B, pool 1, 1.46 W-A; B, pool 2, 1.73 W-A), pea Rubisco LSMT (A, pool 1, 26600 pmoles/min/mg protein; B, pool 1, 26600 pmoles/min/mg protein) and Rubisco carboxylase (A-pea, pool 2, 0.3 µmoles/min/mg protein; B-spinach, pool 1, 2.2 µmoles/min/mg protein). C, Coomassie-blue stained SDS-PAGE (15%; upper panel) and pea Rubisco LSMT immunoanalysis (lower panel) of pooled fractions and enzymes described in B. A duplicate gel as in the upper panel was electroblotted to a PVDF membrane, and probed with protein A-purified anti-pea Rubisco LSMT antibody (1:10000). The pea Rubisco LSMT:HCAII conjugate was of such high molecular mass that the immunoreactive band represents a complex that remained stacked just above the resolving gel such that a Coomassie-blue stained band is not visible in the upper panel.

Example 4

Effect of HCAII Conjugated to Rubisco LSMT on Carboxylase Activity of Spinach and Pea Rubisco Kinetic analyses were performed as described previously for Rubisco Lorimer, G. H., Badger, M. R., and Andrews, T. J. Biochemistry 15, 529-536.1976. Pierce, J. W., McCurry, S. D., Mulligan, R. M., and Tolbert, N. E. Methods Enzymol. 89 Pt D, 47-55.1982. Assays were conducted under $O_2$ free conditions with $CO_2$-free buffers as described below, and contained normalized Rubisco and hCAII activities, unless otherwise indicated. The assays contained, unless otherwise indicated, 100 mM Bicine adjusted to pH 8.2 with a saturated NaOH solution, 20 mM $MgCl_2$, 2 mM dithiothreitol, 0.5 mM RuBP, and $NaH^{14}CO_3$ (1.0 mCi/mmol). Reactions were initiated by the addition of activated Rubisco, or conjugate, injected into an 8 mL serum capped vial (first flushed with nitrogen). Activation of Rubisco or conjugate was performed at 2 mg/mL by incubation at 30 C for 15 min in 50 mM Bicine, pH 8.2, containing 20 mM $MgCl_2$ and 15 mM $NaH^{14}CO_3$. Assay times, enzyme masses, volumes, or specific activities were adjusted to limit substrate consumption to 10% or less. The assays were terminated by the addition by 2N HCl (0.4 volumes), and the liquid evaporated to dryness under a stream of air at 50° C. Radioactivity was determined with a liquid scintillation analyzer (Packard 2000 CA), after addition of 0.5 mL $H_2O$ and 4.5 mL of cocktail (Bio-Safe II, RPI). Enzyme activity was plotted verses substrate concentration and the data fitted to the Michaelis-Menton equation using Sigma Plot version 8.0

Under anaerobic conditions and utilizing $CO_2$-free buffers, the carboxylase activity of spinach Rubisco (6 µg, 15 µM $CO_2$, 1 mM $HCO_3$—, pH 8.2, 0.5 mM RuBP) remains linear until the ~4 nmoles of free $CO_2$ (250 µL assay volume) is consumed yielding a velocity of 0.83 µmoles/min/mg protein (~½ $V_{max}$ of 2.2 µmoles/min/mg protein), and then ceases as $CO_2$ is totally depleted (FIG. 3A). In contrast an equal amount of spinach Rubisco (6 µg) with 0.89 W-A (Wilbur-Anderson units) of CA bound (equivalent to ~300 µg of native unconjugated CA) under identical conditions exhibits linear $CO_2$ fixation for 2 min, at a velocity of 2.08 µmoles/min/mg protein. Addition of an equal amount of CA (300 ng) to control assays has no effect on the profile of $CO_2$ fixation (FIG. 3A). Increasing amounts of free CA to 10-fold more than bound (~3 µg, 10-fold molar excess over Rubisco) resulted in linear $CO_2$ fixation rates over the entire 2 min assay, at a velocity of 0.83 µmoles/min/mg protein. However, a 100-fold increase (also an ~100-fold molar excess over Rubisco) in the amount of free CA resulted in $CO_2$ fixation rates equal to that observed with 300 ng of bound CA. These differences are not observed at saturating levels of $CO_2$, and CA inhibitors abolished the effect of bound CA on carboxylase activity (FIG. 3C). Carboxylase assays at saturating and low $CO_2$ showed no difference in activity between native Rubisco and Rubisco with bound pea Rubisco LSMT alone. Thus, the effect of CA on the carboxylase activity of Rubisco appears to be a consequence of localization through pea Rubisco LSMT binding to Rubisco. An ideal control to substantiate this observation would be an identical conjugate with CA activity that did not bind to Rubisco. The conjugate between pea Rubisco LSMT and CA retains Rubisco LSMT activity, and catalytic methylation of des(methyl) spinach Rubisco by Rubisco LSMT results in release of Rubisco LSMT. Therefore we added 100 µM AdoMet to the Rubisco complex containing bound CA prior to the initiation of carboxylase assays, and the effect of bound CA was abolished (FIG. 3C). Furthermore, Rubisco because it contains a trimethyllysyl residue at position 14 in the LS, and similar experiments with pea Rubisco demonstrated that the pea Rubisco LSMT CA conjugate did not bind to pea Rubisco (FIG. 2A), and no stimulation of carboxylase activity at low $CO_2$ was observed with pea Rubisco (FIG. 3B). The decline in Rubisco carboxylase activity after 1 min was not due to decarbamylation and inactivation of Rubisco, because addition of saturating levels of $CO_2$ after 2 min (15 mM $HCO_3$—) to control assays resulted in velocities of 2.1 µmoles/min/mg protein.

FIG. 3. Assays were conducted under $O_2$ free conditions with $CO_2$-free buffers according to Lorimer, et al., *Biochemistry* 15: 529-536 (1976), altered as described below, and contained equal Rubisco activity and HCAII activity, unless otherwise indicated. The assays contained 100 mM Bicine adjusted to pH 8.2 with a saturated NaOH solution, 20 mM $MgCl_2$, 2 mM dithiothreitol, 0.5 mM RuBP, and 15 μM $NaH^{14}CO_3$ (499-573 dpm/nmole). Reactions were initiated by the addition of 6 μg of activated Rubisco, (activated at 2 mg/mL by incubation at 30° C. for 15 min in 50 mM Bicine, pH 8.2, containing 20 mM $MgCl_2$ and 15 mM $NaH^4CO_3$, (499-573 dpm/nmole), injected into an 8 mL serum-capped vial (first flushed with nitrogen). The assays were conducted in a volume of 0.25 mL, terminated by the addition of 0.1 mL of 2 N HCl, and the liquid evaporated to dryness under a stream of air at 50° C. Radioactivity was determined with a liquid scintillation analyzer (Packard 2000 CA), after the addition of 0.5 mL $H_2O$ and 4.5 mL of scintillation cocktail (Bio-Safe II, RPI). A, Acid-stable incorporation of $^{14}CO_2$ with time with spinach Rubisco (6 μg; Vmax=2.2 μmoles $CO_2$/min/mg protein) with and without pea Rubisco LSMT:HCAII conjugate (6 μg Rubisco, 0.9 W-A, equivalent to 0.3 μg HCAII) or 0.3 (1×), 3.0 (10×), and 30 μg (100×) of free HCAII. Inset, Spinach Rubisco with pea Rubisco LSMT:HCAII conjugate preincubated with AdoMet (100 μM) or HCA II inhibitors (1.5 mM ampicillin and 0.5 mM acetazolamide). B, Same condition as A but with pea Rubisco (46 μg, Vmax=0.3 μmoles $CO_2$/min/mg protein) with and without pea Rubisco LSMT:HCAII conjugate (0.9 W-A, equivalent to 0.3 μg HCAII) or 0.3 μg HCAII (1×).

FIG. 4 illustrates the kinetic analyses of Rubisco, Rubisco complexed with hCA, and Rubisco complexed with hCA in the presence of acetazolamide (Az).

A mathematical consideration of the potential proximity effect of CA in these assays suggest that a maximum of ~41-fold could be observed in terms of a decrease in the diffusion distance between $CO_2$ formed at the active-site of soluble CA compared to CA bound to Rubisco assuming a mean hydrodynamic radius of ~50 Å for the distance of bound CA from the active-site of Rubisco (structural dimensions of HCAII a=43 Å, b=42 Å, c=73 Å). At 6 μg/250 μL the concentration of Rubisco is 45 nM (~534,000 daltons). Free concentrations of CA at 0.3, 3, and 30 μg/250 μL represent 41, 410, and 4100 nM (~29,000 daltons). The molecular density of Rubisco at 45 nM is $2.7 \times 10^{10}$ molecules/mm³. Therefore the solution volume occupied by a single molecule of Rubisco at 45 nM is $3.7 \times 10^{10}$ Å3, and a sphere containing this volume has a radius of 2067 Å. If CA bound to Rubisco is within ~50 Å (averaged dimensions of a CA tetrahedral) of the active-site then the ratio of the maximum distance between bound and free CA is ~41-fold. While the effectiveness of bound CA was mimicked by 30 μg of unbound CA, and thus the efficiency of bound CA is 100-fold greater, this effect has not been titrated and may therefore be overestimated, thus reducing the actual efficiency increase. Nevertheless, clearly the possibility exist that CA targeted to Rubisco has increased efficiency for supporting carboxylase activity at low $CO_2$, by facilitating equilibrium between $HCO_3^-$ and $CO_2$ in direct proximity to the active site of Rubisco. However, the nearly saturated levels of carboxylase activity in the presence of conjugated bound CA, and the 100-fold molar excess of free CA, is not readily explainable. This effect would presumably be manifested by a lowering of the $_{app}K_m$ $(CO_2)$, but again how this might be accomplished is not clear. Perhaps the CA catalyzed equilibrium between $HCO_3^-$ and $CO_2$ in proximity to Rubisco results in a temporary increase in $CO_2$ above that which would be present with free CA, and the effects of a 100-fold molar excess of CA mimic this effect through such a large enzyme concentration. The possibility that such a large molar excess of free CA relative to Rubisco resulted in some non-specific protein association was addressed by incubation of CA and Rubisco at these ratios and subsequent gel-filtration on Sepharose 6B as shown in FIG. 2. The results indicated no association between Rubisco and CA even at a 100:1 molar ratio.

Example 5

Construction and Purification of RLSMT-CA Fusion Protein

Figure 5:
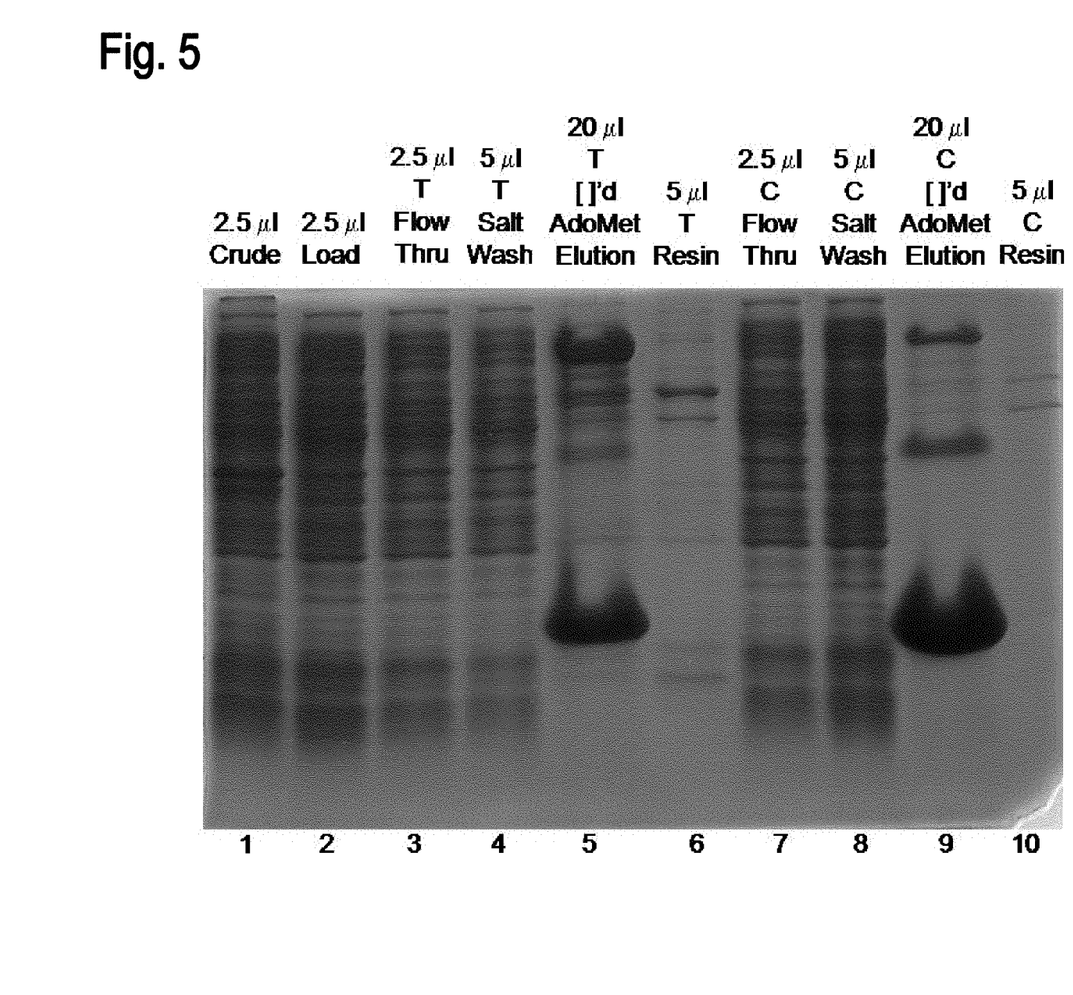
FIG. 5 illustrates the purification of RLSMT-CA fusion protein.

The RLSMT Carbonic Anhydrase (RLSMT-CA) fusion was constructed in a pET vector from Stratagene. The nucleic acid sequence encoding carbonic anhydrase (Accession number NM_000067) was fused to the carboxyl terminus of Pea RLSMT (Accession number Q43088), and cloned into the pET vector using pET vector protocols from Stratagene and other standard molecular biology protocols. SEQ ID No.: 1 is the nucleic acid sequence of the RLSMT-CA. SEQ ID No.: 2 is the amino acid sequence of the RLSMT-CA fusion protein. Again, using standard molecular biology protocols, this pET-RLSMT-CA vector was transformed into *E. coli*. *E. coli* expressing the pET-RLSMT-CA vector were cultured under conditions suitable for expression of the RLSMT-CA fusion protein. ~130 ml of this culture was pelleted, washed, and lysed using standard protocols. This lysate was resuspended in 5 ml standard buffer. 2.5 ml of this solution was loaded onto ~0.5 ml packed Spinach-Rubisco-conjugated activated Thiol-Sepharose 4B (T). 2.5 ml of this solution was loaded onto ~1.0 ml packed Spinach-Rubisco-conjugated Cyanogen bromide-Activated Sepharose (C). The resin was washed with 40 ml of 0.4 M NaCl in standard buffer. RLSMT-CA eluted with AdoMet: about ~3 h with 100 μM AdoMet in standard buffer with 100 μg/ml β-lactoglobulin (0.5 ml for T and 1.0 ml for C); concentrated with YM50. A Coomassie blue stained SDS-PAGE gel illustrating the elution of the RLSMT-CA is shown in FIG. 5. The Rubisco LSMT-CA fusion protein eluted in lanes 5 and 9 contained 22.3 pmoles/min/μl of Rubisco methyltransferase activity and 0.007-0.034 Abs/sec/μl of carbonic anhydrase activity.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The invention claimed is:

1. A modified Rubisco large subunit ᵉN-methyltransferase (RLSMT), comprising a Rubisco large subunit ᵉN-methyltransferase linked to a second molecule and wherein the modified RLSMT has the ability to bind a Rubisco.

2. The modified RLSMT of claim 1, wherein the Rubisco large subunit ᵉN-methyltransferase is linked to the second molecule by a chemical.

3. The modified RLSMT of claim 2, wherein the chemical is glutaraldehyde.

4. The modified RLSMT of claim 2, wherein the modified RLSMT is a fusion protein, wherein the fusion protein is encoded by a nucleic acid, wherein the nucleic acid comprises a first nucleic acid encoding a Rubisco large subunit ᵉN-methyltransferase, and wherein the nucleic acid further comprises a second nucleic acid encoding a polypeptide.

5. The modified RLSMT of claim 1, wherein the second molecule is carbonic anhydrase.

6. The modified RLSMT of claim 1, wherein the second molecule is a phosphatase, 3-phosphoglycerate kinase, glyceraldehydes-3-phosphate dehydrogenase, Rubisco Activase, Phosphoribulokinase, polylysine, or oxygenase.

7. The modified RLSMT of claim 1, wherein the modified RLSMT is a fusion protein, wherein the fusion protein is encoded by a nucleic acid.

8. A modified Rubisco large subunit $\epsilon$N-methyltransferase of claim 1, wherein said second molecule is a carbonic anhydrase, wherein the modified RLSMT (RLSMT-CA) has the ability to bind a Rubisco large subunit.

9. The modified RLSMT of claim 8, wherein the Rubisco large subunit $\epsilon$N-methyltransferase is linked to the carbonic anhydrase (CA) by a chemical.

10. The modified RLSMT of claim 9, wherein the chemical is glutaraldehyde.

11. The modified RLSMT of claim 8, wherein the modified RLSMT is a fusion protein, wherein the fusion protein is encoded by a nucleic acid, wherein the nucleic acid comprises a first nucleic acid encoding a Rubisco large subunit $\epsilon$N-methyltransferase, and wherein the nucleic acid further comprises a second nucleic acid encoding a carbonic anhydrase.

12. The modified RLSMT of claim 8, wherein the modified RLSMT further comprises an antibody.

13. The modified RLSMT of claim 11, wherein the antibody is linked to a CA.

14. The modified RLSMT of claim 8 comprising SEQ ID No.: 2.

* * * * *

SEQUENCE LISTING

```
<160> NUMBER OF SEQ ID NOS: 2

<210> SEQ ID NO 1
<211> LENGTH: 2181
<212> TYPE: DNA
<213> ORGANISM: artificial sequence
<220> FEATURE:
```

<223> OTHER INFORMATION: RLSMT-CA fusion

<400> SEQUENCE: 1

```
atggcaaaat cagtagcctc tgtaggaacc gaaccatcac tgtctccagc agttcaaacc    60
ttctggaagt ggctacagga agaaggtgtc atcactgcaa agaccccagt gaaagctagt   120
gtggtcacag aaggtttagg attggttgca cttaaggaca tttctaggaa tgatgttatt   180
ttgcaggtac caaaaaggct gtggataaat ccagatgcag ttgcagcttc agagattggg   240
agagtgtgca gtgagttgaa gccatggttg tctgttatac tctttcttat aagagagagg   300
tcaagggaag attctgtttg gaagcactat tttggtattc tgccacagga aactgattct   360
actatatatt ggtcagagga agagcttcaa gagcttcaag ttctcaact tttgaaaaca   420
acagtgtctg tgaaagaata tgtgaagaat gaatgtttga actagaaaca agaaatcatt   480
ctccctaata agcggctttt tccggatcct gtgacgctgg atgacttctt ttgggcattt   540
ggaattctca gatcaagggc gttttctcgc cttcgcaatg aaaatctggt tgtggttcca   600
atggcagact tgattaacca cagtgcagga gttactacag aggatcatgc ttatgaagtt   660
aaaggagcag ctggcctttt ctcttgggat tacctatttt ccttaaagag ccccctttcc   720
gtcaaggccg gagaacaggt atatatacaa tatgatttga acaaaagcaa tgcagagttg   780
gctctagact acggtttcat tgaaccaaat gaaaatcgac atgcatacac tctgacgctg   840
gagatatctg agtcggaccc ttttttgat gacaaactag acgttgctga gtccaatggt   900
tttgctcaga cagcgtactt tgacatcttc tataatcgca ctcttccacc tggattgctt   960
ccatatctga gacttgtagc gctaggggt accgacgctt tcttattgga atcactgttc   1020
agagacacca tatggggtca tcttgagttg tctgtcagcc gtgacaatga ggagctacta  1080
tgcaaagccg ttcgagaagc ctgcaaatct gcccttgctg ttatcatac aaccattgaa   1140
caggatcgcg agttgaaaga aggaaatcta gattcaaggc ttgcaatagc agttggaata   1200
agagaagggg aaaagatggt cctgcagcaa attgacggga tcttcgagca gaaagaattg  1260
gagttggacc agttagagta ttatcaagaa aggaggctca aggatcttgg actttgcgga  1320
gaaaatggcg atatccttgg agacctagga aaattcttcc tcgaaggcgg aggcgggagc  1380
gcggccgcgg gcagcctcga gtcccatcac tgggggtacg gcaaacacaa cggacctgag  1440
cactggcata aggacttccc cattgccaag ggagagcgcc agtcccctgt tgacatcgac   1500
actcatacag ccaagtatga cccttccctg aagcccctgt ctgtttccta tgatcaagca  1560
acttccctga ggatcctcaa caatggtcat gcttttcaacg tggagtttga tgactctcag  1620
gacaaagcag tgctcaaggg aggacccctg gatggcactt acagattgat tcagtttcac  1680
tttcactggg gttcacttga tggacaaggt tcagagcata ctgtggataa aagaaatat  1740
gctgcagaac ttcacttggt tcactggaac accaaatatg gggattttgg gaaagctgtg  1800
cagcaacctg atggactggc cgttctaggt atttttttga aggttggcag cgctaaaccg  1860
ggccttcaga agttgttga tgtgctggat tccattaaaa caaagggcaa gagtgctgac  1920
ttcactaact cgatcctcg tggcctcctt cctgaatccc tggattactg gacctaccca  1980
ggctcactga ccaccccctcc tcttctggaa tgtgtgacct ggattgtgct caaggaaccc  2040
atcagcgtca gcagcgagca ggtgttgaaa ttccgtaaac ttaacttcaa tggggagggt  2100
gaacccgaag aactgatggt ggacaactgg cgcccagctc agccactgaa gaacaggcaa  2160
atcaaagctt ccttcaaata a                                             2181
```

<210> SEQ ID NO 2

<211> LENGTH: 728
<212> TYPE: PRT
<213> ORGANISM: artificial sequence
<220> FEATURE:
<223> OTHER INFORMATION: RLSMT-CA fusion protein

<400> SEQUENCE: 2

| | | | | | | | | | | | | | | |
|---|---|---|---|---|---|---|---|---|---|---|---|---|---|---|
| Met | Ala | Lys | Ser | Val | Ala | Ser | Val | Gly | Thr | Glu | Pro | Ser | Leu | Ser | Pro |
| 1 | | | | 5 | | | | | 10 | | | | | 15 | |
| Ala | Val | Gln | Thr | Phe | Trp | Lys | Trp | Leu | Gln | Glu | Glu | Gly | Val | Ile | Thr |
| | | | 20 | | | | | 25 | | | | | 30 | | |
| Ala | Lys | Thr | Pro | Val | Lys | Ala | Ser | Val | Val | Thr | Glu | Gly | Leu | Gly | Leu |
| | | 35 | | | | | 40 | | | | | 45 | | | |
| Val | Ala | Leu | Lys | Asp | Ile | Ser | Arg | Asn | Asp | Val | Ile | Leu | Gln | Val | Pro |
| | 50 | | | | | 55 | | | | | 60 | | | | |
| Lys | Arg | Leu | Trp | Ile | Asn | Pro | Asp | Ala | Val | Ala | Ser | Glu | Ile | Gly |
| 65 | | | | | 70 | | | | 75 | | | | | 80 |
| Arg | Val | Cys | Ser | Glu | Leu | Lys | Pro | Trp | Leu | Ser | Val | Ile | Leu | Phe | Leu |
| | | | | 85 | | | | | 90 | | | | | 95 | |
| Ile | Arg | Glu | Arg | Ser | Arg | Glu | Asp | Ser | Val | Trp | Lys | His | Tyr | Phe | Gly |
| | | | 100 | | | | | 105 | | | | | 110 | | |
| Ile | Leu | Pro | Gln | Glu | Thr | Asp | Ser | Thr | Ile | Tyr | Trp | Ser | Glu | Glu | Glu |
| | | 115 | | | | | 120 | | | | | 125 | | | |
| Leu | Gln | Glu | Leu | Gln | Gly | Ser | Gln | Leu | Leu | Lys | Thr | Thr | Val | Ser | Val |
| | 130 | | | | | 135 | | | | | 140 | | | | |
| Lys | Glu | Tyr | Val | Lys | Asn | Glu | Cys | Leu | Lys | Leu | Glu | Gln | Glu | Ile | Ile |
| 145 | | | | | 150 | | | | | 155 | | | | | 160 |
| Leu | Pro | Asn | Lys | Arg | Leu | Phe | Pro | Asp | Pro | Val | Thr | Leu | Asp | Asp | Phe |
| | | | | 165 | | | | | 170 | | | | | 175 | |
| Phe | Trp | Ala | Phe | Gly | Ile | Leu | Arg | Ser | Arg | Ala | Phe | Ser | Arg | Leu | Arg |
| | | | 180 | | | | | 185 | | | | | 190 | | |
| Asn | Glu | Asn | Leu | Val | Val | Val | Pro | Met | Ala | Asp | Leu | Ile | Asn | His | Ser |
| | | | 195 | | | | | 200 | | | | | 205 | | |
| Ala | Gly | Val | Thr | Thr | Glu | Asp | His | Ala | Tyr | Glu | Val | Lys | Gly | Ala | Ala |
| | | 210 | | | | | 215 | | | | | 220 | | | |
| Gly | Leu | Phe | Ser | Trp | Asp | Tyr | Leu | Phe | Ser | Leu | Lys | Ser | Pro | Leu | Ser |
| 225 | | | | | 230 | | | | | 235 | | | | | 240 |
| Val | Lys | Ala | Gly | Glu | Gln | Val | Tyr | Ile | Gln | Tyr | Asp | Leu | Asn | Lys | Ser |
| | | | | 245 | | | | | 250 | | | | | 255 | |
| Asn | Ala | Glu | Leu | Ala | Leu | Asp | Tyr | Gly | Phe | Ile | Glu | Pro | Asn | Glu | Asn |
| | | | 260 | | | | | 265 | | | | | 270 | | |
| Arg | His | Ala | Tyr | Thr | Leu | Thr | Leu | Glu | Ile | Ser | Glu | Ser | Asp | Pro | Phe |
| | | 275 | | | | | 280 | | | | | 285 | | | |
| Phe | Asp | Asp | Lys | Leu | Asp | Val | Ala | Glu | Ser | Asn | Gly | Phe | Ala | Gln | Thr |
| | 290 | | | | | 295 | | | | | 300 | | | | |
| Ala | Tyr | Phe | Asp | Ile | Phe | Tyr | Asn | Arg | Thr | Leu | Pro | Pro | Gly | Leu | Leu |
| 305 | | | | | 310 | | | | | 315 | | | | | 320 |
| Pro | Tyr | Leu | Arg | Leu | Val | Ala | Leu | Gly | Gly | Thr | Asp | Ala | Phe | Leu | Leu |
| | | | | 325 | | | | | 330 | | | | | 335 | |
| Glu | Ser | Leu | Phe | Arg | Asp | Thr | Ile | Trp | Gly | His | Leu | Glu | Leu | Ser | Val |
| | | | 340 | | | | | 345 | | | | | 350 | | |
| Ser | Arg | Asp | Asn | Glu | Glu | Leu | Leu | Cys | Lys | Ala | Val | Arg | Glu | Ala | Cys |
| | | 355 | | | | | 360 | | | | | 365 | | | |
| Lys | Ser | Ala | Leu | Ala | Gly | Tyr | His | Thr | Thr | Ile | Glu | Gln | Asp | Arg | Glu |
| | 370 | | | | | 375 | | | | | 380 | | | | |

```
Leu Lys Glu Gly Asn Leu Asp Ser Arg Leu Ala Ile Ala Val Gly Ile
385                 390                 395                 400

Arg Glu Gly Glu Lys Met Glu Thr Val Leu Gln Gln Ile Asp Gly Ile
                405                 410                 415

Phe Glu Gln Lys Glu Leu Glu Leu Asp Gln Leu Glu Tyr Tyr Gln Glu
                420                 425                 430

Arg Arg Leu Lys Asp Leu Gly Leu Cys Gly Glu Asn Gly Asp Ile Leu
                435                 440                 445

Gly Asp Leu Gly Lys Phe Phe Leu Glu Gly Gly Gly Ser Ala Ala
        450                 455                 460

Ala Gly Ser Leu Glu Ser His His Trp Gly Tyr Gly Lys His Asn Gly
465                 470                 475                 480

Pro Glu His Trp His Lys Asp Phe Pro Ile Ala Lys Gly Glu Arg Gln
                485                 490                 495

Ser Pro Val Asp Ile Asp Thr His Thr Ala Lys Tyr Asp Pro Ser Leu
                500                 505                 510

Lys Pro Leu Ser Val Ser Tyr Asp Gln Ala Thr Ser Leu Arg Ile Leu
                515                 520                 525

Asn Asn Gly His Ala Phe Asn Val Glu Phe Asp Asp Ser Gln Asp Lys
530                 535                 540

Ala Val Leu Lys Gly Gly Pro Leu Asp Gly Thr Tyr Arg Leu Ile Gln
545                 550                 555                 560

Phe His Phe His Trp Gly Ser Leu Asp Gly Gln Gly Ser Glu His Thr
                565                 570                 575

Val Asp Lys Lys Lys Tyr Ala Ala Glu Leu His Leu Val His Trp Asn
                580                 585                 590

Thr Lys Tyr Gly Asp Phe Gly Lys Ala Val Gln Gln Pro Asp Gly Leu
                595                 600                 605

Ala Val Leu Gly Ile Phe Leu Lys Val Gly Ser Ala Lys Pro Gly Leu
        610                 615                 620

Gln Lys Val Val Asp Val Leu Asp Ser Ile Lys Thr Lys Gly Lys Ser
625                 630                 635                 640

Ala Asp Phe Thr Asn Phe Asp Pro Arg Gly Leu Leu Pro Glu Ser Leu
                645                 650                 655

Asp Tyr Trp Thr Tyr Pro Gly Ser Leu Thr Thr Pro Pro Leu Leu Glu
                660                 665                 670

Cys Val Thr Trp Ile Val Leu Lys Glu Pro Ile Ser Val Ser Ser Glu
                675                 680                 685

Gln Val Leu Lys Phe Arg Lys Leu Asn Phe Asn Gly Glu Gly Glu Pro
                690                 695                 700

Glu Glu Leu Met Val Asp Asn Trp Arg Pro Ala Gln Pro Leu Lys Asn
705                 710                 715                 720

Arg Gln Ile Lys Ala Ser Phe Lys
                725
```